United States Patent [19]

Weil

[11] 4,059,615

[45] Nov. 22, 1977

[54] SIDE CHAIN HALOGENATED ALKYLPHENYL HALOFORMATES AND DERIVATIVES

[75] Inventor: Edward D. Weil, Hastings-on-Hudson, N.Y.

[73] Assignee: Hooker Chemicals & Plastics Corporation, Niagara Falls, N.Y.

[21] Appl. No.: 658,792

[22] Filed: Feb. 17, 1976

Related U.S. Application Data

[60] Continuation of Ser. No. 19,516, March 13, 1970, abandoned, which is a continuation-in-part of Ser. No. 816,426, Nov. 7, 1968, Pat. No. 3,651,129, which is a division of Ser. No. 305,509, Aug. 29, 1963, Pat. No. 3,420,868.

[51] Int. Cl.$^2$ .......................................... C07C 125/06

[52] U.S. Cl. ............................. 560/132; 260/463; 560/137

[58] Field of Search ................................. 260/479 C

[56] References Cited

U.S. PATENT DOCUMENTS 3,470,236  6/1965  Hansweiler et al. ............. 260/479 C Primary Examiner—Natalie Trousof
Assistant Examiner—Jane T. Fan
Attorney, Agent, or Firm—P. F. Casella; W. J. Crossetta; A. S. Cookfair

[57] ABSTRACT

This invention relates to novel α-lower alkoxy-o-cresyl carbamates having utility as insecticides and polymer intermediates.

1 Claim, No Drawings

SIDE CHAIN HALOGENATED ALKYLPHENYL HALOFORMATES AND DERIVATIVES

This is a continuation, of application Ser. No. 19,516, filed Mar. 13, 1970, now abandoned, which was a continuation-in-part of Ser. No. 816,426, filed November 7, 1968, now U.S. Pat. 3,651,129, which was a division of Ser. No. 305,509, filed Aug. 29, 1963, now U.S. Pat. No. 3,420,868.

This invention relates to new compositions of matter and to processes for making them. More specifically, the invention relates to a new class of compounds designated as side chain halogenated alkylphenyl haloformates, O-(alkylaryl) carbamate esters possessing reactive bromine or chlorine atoms on the side chain, which may be derived from the haloformates, and to processes for the preparation thereof.

The haloformate compounds of such compositions of the present invention find utility as pesticides, pesticide intermediates, polymer intermediates, and chemical intermediates which are especially useful for the preparation of side chain halogenated phenols and side chain halogenated phenyl carbamates, carbonates, and other esters.

It is an object of the haloformate aspect of the invention to make available difunctional and higher functional monomeric compounds which, by replacement of two or more reactive halogen atoms by means of a difunctional or higher polyfunctional nucleophilic reagent, will yield useful polymers.

It is a further object to produce compounds which have biocidal and cytostatic activity, for use in pest control and growth retardation of living matter.

Another object is to make available chemical intermediates which can readily be converted to side chain halogenated phenols and their derivatives which have not hither to been available.

It is still a further object to make chemical intermediates which, by reaction with ammonia, primary amines, or secondary amines, yield pesticidal carbamates, and which, by reaction with alcohols, yield pesticidal carbonates.

It is another object of the present invention to make available a series of versatile chemical intermediates capable of reaction with a great variety of nucleophilic reagents without destruction of the carbamate linkage, and thus giving access to many series of new and useful carbamate derivatives not otherwise available.

A further object of the invention is to make available a series of new carbamates having diverse pesticidal, biocidal and bio-regulatory activity per se.

Another object is to make available convenient processes for manufacture of such compounds.

These and other objects of the invention will become apparent from a further reading of this specification.

The novel compounds of the present invention are represented by the following formula:

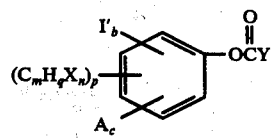

wherein the substituents:

1. X and X' are halogens of atomic weight between 34 and 81;
2. A is an alkyl radical, preferably of from 1 to about 6 carbon atoms;
3. $b$ is from 0 to (5-$p$), inclusive;
4. $c$ is from 0 to (5-$p$-$b$), inclusive;
5. $m$ is from 1 to 20;
6. $n$ is from 1 to $2m+1$;
7. $p$ is from 1 to 5;
8. $q$ is equal to the remaining number of valences on the radical $C_mH_qX_n$;
9. Y is selected from the group consisting of (a) halogens of atomic weight between 34 and 81, (b) the radical represented by the formula

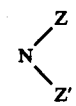

wherein Z and Z' are selected from the group consisting of hydrogen, hydrocarbyl, hydrocarbyl substituted by hydroxy, halogen, nitro, and may be conjoined by a carbon-to-carbon bond or by an imino-, sulfur or oxygen and (c) the radical represented by the formula QR wherein Q is an element of Group VI of the Periodic Table having an atomic weight between 15 and 33 and R is selected from the group consisting of alkyl, haloalkyl, phenyl, nitrated phenyl, and dialkoxythiophenylthio.

By the term "hydrocarbyl" is meant the radical obtained by removal of one hydrogen atom from a hydrocarbon and thus encompasses alkyl, alkenyl, aryl, cycloalkyl, cycloalkenyl, and arylalkyl.

The novel side chain halogenated alkylphenyl haloformate compounds of the present invention are represented by the following formula:

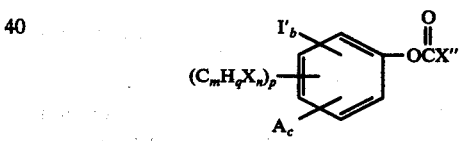

wherein the substituents:

1. X, X', X" are halogens of atomic weight between 34 and 81;
2. A is an alkyl substituent, preferably of from 1 to about 6 carbon atoms;
3. $b$ is from 0 to (5-p) inclusive;
4. $c$ is from 0 to (5-p-b) inclusive;
5. $m$ is from 1 to about 20;
6. $n$ is from 1 to $2m+1$;
7. $p$ is from 1 to 5; and
8. $q$ is equal to the remaining number of valences on the group $C_{mHq}X_n$.

The term "alkyl" is intended to encompass cycloalkyl and alkyls substituted by non-interfering substituents. The $C_mH_qX_n$ groups may also be joined to the benzene ring at the adjacent carbon atom of said benzene ring, thus forming a cycloaliphatic ring fused to the benzene ring. The referred halogenated alkylphenyl haloformates of the invention for reasons of cost are those wherein the substituent:

1. X" is chlorine,
2. $n$ is from 1 to 4, inclusive, 3. $p$ is from 1 to 2, inclusive; and 4. C is 0, where more than 1 halogen atoms is attached to any single carbon atom on the group $C_mH_qX_n$.

A number of O-aryl carbamates have been known which have halogen atoms directly on the aromatic ring. However, such compounds are of no value as chemical intermediates to produce new carbamates, since the ring halogen atoms are inert and cannot be replaced, at least not without degradation of the carbamate linkage.

More specifically, the novel side chain halogenated alkylphenyl carbamates of the invention are represented by the formula:

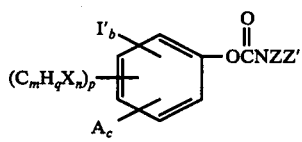

wherein the substituent;

1. X and X' are halogen of atomic weight from 34 to 81;
2. m is an integer from 1 to about 20;
3. p is a integer from 1 to 5;
4. b is a integer from 0 to (5-p) inclusive;
5. c is an integer from p to (5-p-b), inclusive;
6. q equals the remaining valences of the group $C_mH_qX_n$;
7. A is an alkyl substituent; and
8. Z and Z' are radicals selected from the group consisting of hydrogen, hydrocarbyl, hydrocarbyl substituted by hydroxy, halogen or nitro, and where both Z and Z' may be conjoined by a carbon-to-carbon bond or by an imino, sulfur, or oxygen bridge. The $C_mH_qX_n$ group may optionally be joined to the benzene ring at two adjacent carbon atoms of the bezene ring, thus forming a cycloaliphatic ring fused to the benzene ring.

The preferred embodiments for reasons of cost and efficacy are those in which n is an integer from 1 to 4, p is a integer from 1 to 2 inclusive, c is 0, where more than 1 halogen atom is attached to any single carbon atom of the group $C_mH_qX_n$, and Z and Z' when individual radicals represent a member of the class comprising hydrogen, hydrocarbyl, hydroxyl substituted hydrocarbyl, halogen-substituted hydrocarbyl and nitro-substituted hydrocarbyl and when said Z and Z' radicals are joined, they represent together with the nitrogen atom to which they are attached, a heterocyclic radical selected from the group consisting of piperidyl, morpholinyl and 1-aziridinyl.

There are preferred subgroups, each of which has its particular area of greatest utility. In the present invention, several such carbamate subgroups (chosen on the basis of utility) may be described:

a. compounds of the preferred group as described above, wherein Z and Z' are chosen from hydrogen and lower alkyl (1 to 5 carbons), or wherein NZZ' represents aziridinyl or 1-morpholinyl, have the highest degree of nematocidal and insecticidal activity, as well as the greatest utility as insecticide intermediates. Of this group, the most active per se are those wherein Z is methyl, Z' is hydrogen, b is zero, p is an integer from 1 to 2, m is an integer from 1 to about 6, n is an integer from 1 to 4, A is a lower alkyl (having up to 6 carbon atoms), and at least one position ortho to the ester side chain is unsubstituted.

b. compounds of the preferred group as described above wherein Z is hydrogen and Z' is phenyl, halogenated phenyl, nitrophenyl, and naphthyl, are most active as antimicrobial agents, and are also useful against higher plant organisms.

Viewed from the alternative standpoint of low cost, ease of synthesis and superior yield, those compounds within the scope of the invention wherein $C_mH_qX_n$ represents $CH_2X$, $CHX_2$ or $CX_3$ are especially advantageous since methylphenyl haloformates are available inexpensively and the methyl side chain (having only a single carbon) does not permit position isomerism in the halogenation. Also advantageous for the same reasons are those compounds wherein $C_mH_qX_n$ represent a $-CH_2CHXCH_2X$ group in the ortho position to the ester linkage; this group is produced in excellent yield from readily available o-allylphenyl haloformates by the addition of halogen to the allyl group under the conditions of the process of the invention.

Illustrative examples of the ($C_mH_qX_n$) grouping include chloromethyl, dichloromethyl, trichloromethyl, bromomethyl, dibromomethyl, bromomethyl, dibromoethyl, 1-chloroethyl, 2-chloroethyl, 1,1-dichloropropyl, 1,2-dichloropropyl, 1,2,3-trichloropropyl, 2,3-dichloropropyl, 2,3-dibromopropyl, dichlorobutyl, chloroisobutyl, chloro-sec-butyl, 1-chlorocyclohexyl, 2,3-dichlorocyclopentyl, trichlorooctyl, chlorooctadecyl, chloreicosyl, dichloropentadecyl, tetrachloropentadecyl, chlorocyclooctyl, bromocyclooctyl, chlorocyclobutyl, bromocyclobutyl, and the like. Where p is greater than 0, the several ($C_mH_qX_n$) groups may differ from one another, as may the several X groups and/or X' groups, when b and/or c are greater than 1.

Among the alkyl substituents which generally contain from 1 to about 20 carbon atoms are methyl, ethyl, isopropyl, propyl, butyl, sec-butyl, isobutyl, tert-butyl, amyl, isoamyl, sec-amyl, hexyl, 1-ethylbutyl, eicosyl, and the like. The preferred alkyl groups contain from 1 to about 6 carbon atoms.

Illustrative examples of the halogenated alkylphenyl haloformate compounds included in the present invention are:

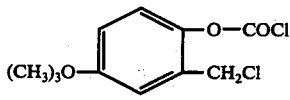
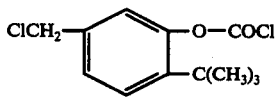
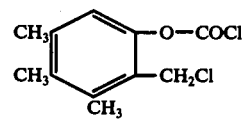
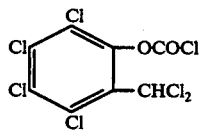
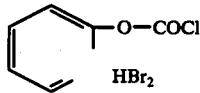
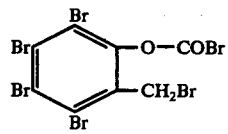

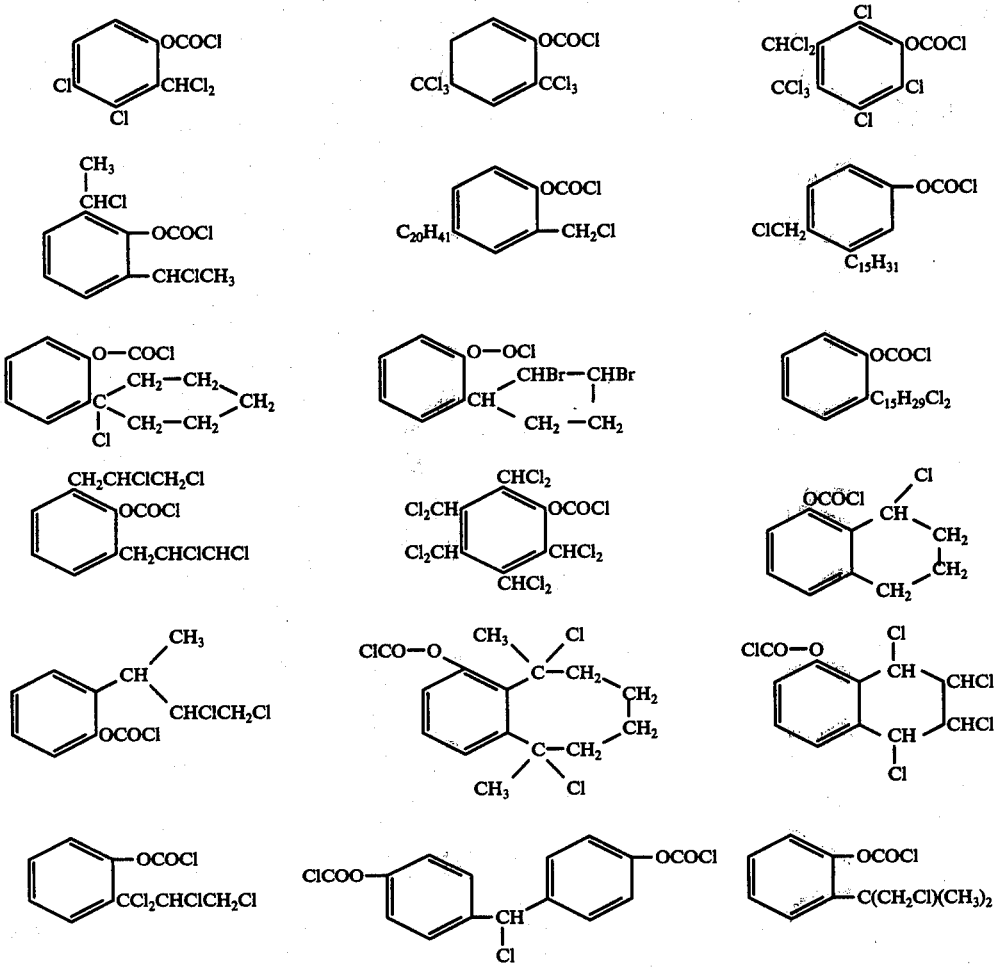

Several subgroups may be distinguished among the haloformates of the invention. Those compounds wherein m is 1 and n is 1 have the reactive benzyl-type halogen atom, and thus are especially useful as reactive intermediates toward nucleophiles and as polymer intermediates. Where there are more than one such —CH$_2$X group, the compounds are polyfunctional alkylating agents. Where two —CH$_2$X groups are adjacent on the ring, the compounds are intermediates for heterocyclic syntheses.

The compounds having —CHX$_2$ groups are useful intermediate for hydrolysis to aldehydes. The compounds having —CX$_3$ groups are useful intermediates for hydrolysis to carboxylic acids. The compounds having —CH$_2$CHXCH$_2$X side chains are generally more stable halogen and are also useful for synthesis of long-lasting pesticides. The compounds having —CHX$_2$ groups can be reacted with amines and then with mercaptides to make α,α-bis(hydrocarbylthio)methylphenyl carbamate insecticides.

Representative examples of carbamates within the scope of the invention include the following:

α-bromo-o-cresyl carbamate
α,α-dichloro-5-bromo-o-cresyl N-methylcarbamate
m-(tetrachloropentadecyl) phenyl N-methylcarbamate
α, β, β, β'-tetrachloro-m-isopropylphenyl N-methylcarbamate
α-chloro-o-eicosylphenyl N-methylcarbamate
α, α, 3,4,5,6-hexachloro-o-cresyl N-cyclopentylcarbamate
4-(chloromethyl)-2,3,5,6-tetramethylphenyl N,N-dimethylcarbamate
α, α'-dichloro-2,4-xylenyl N,N-di(2-hydroxyethyl) carbamate
penta(chloromethyl) phenyl N,N-di(2-chloroethyl) carbamate
α, α-dichloro-o-cresyl N-naphthylcarbamate
α3,4-trichloro-o-cresyl N-(p-nitrophenyl) carbamate
α, α, α, 4,6-pentachloro-o-cresyl N(3,4-dichlorophenyl) carbamate
α, α, α-tribromo-p-cresyl N-propargylcarbamate
2-(2,3-dichloropropyl) phenyl thiomorpholine-N-carboxylate
α, α'-dichloro-3,5-xylenyl piperazine-N-carboxylate
α, α-dibromo-o-cresyl N-(2-chloro-5-cyclooctenyl)carbamate
α, α', 4,6-tetrachloro-2,3-xylenyl N,N-diallylcarbamate
α-chloro-2-cyclohexylphenyl N-benzylcarbamate
bis(α-chloro-p-cresyl) ethylene-N,N'-dicarboxylate
2-bromo-4-(chloromethyl)-6-nonylphenyl piperidine-N-carboxylate
α, α, α-trichloro-m-cresyl pentamethylenimine-N-carboxylate
2-(2,3-dibromopropyl)-o-cresyl N-methylcarbamate
2,4-bis(2,3-dichlorobutyl)-m-cresyl N-1-anthracylcarbamate as well as fused ring compounds such as:

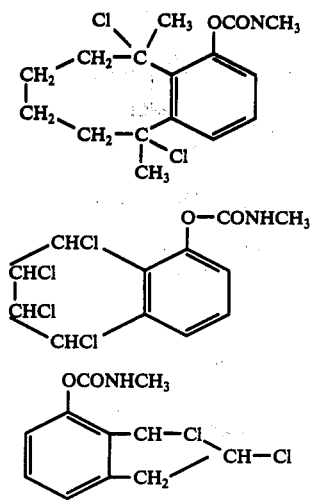

and the like. Further examples are given hereinafter.

Novel compounds of the present invention may be prepared by the halogenation of the corresponding haloformates of the formula:

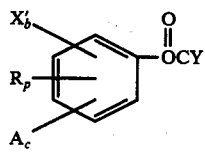

in which R is a saturated or olefinic hydrocarbyl radical of the same carbon skeleton as the $C_mH_qX_n$ group to be produced, and X', A, m and c are as defined herein, and Y is a halogen atom of atomic weight between 34 and 81, utilizing to said halogenation about n molar equivalents of the halogenating agent under suitable conditions described below, followed by isolation of the desired haloformate or further reaction of said haloformate, with an amine of the formula HNZZ' wherein Z and Z' are as defined herein.

Where R is a saturated group, a molar equivalent of a halogenating agent will be sufficient to remove one gram-atom of hydrogen and replace said gram-atom of hydrogen with one X gram-atom. Where R is an olefinic group, a molar equivlalent of halogenating agent wil be that which introduces one gram-atom of halogen (X). Obviously, when R is olefinic, the first halogen atoms will enter two at a time by addition to the double bond and n will have minimum value of 2.

By "halogenating agent" is meant the free halogen or any equivalent halogenating agent capable of yielding up its halogen under free radical reaction condition, for example, sulfuryl chloride, phosphorus pentachloride, phosphorus pentabromide, N-chloro- and N-bromo amines and amides such as N-chlorobenzamide, N-bromosuccinimide, N,N'-dibromodimethylhydantoin, N,N'-dichlorodimethylhydantoin, N-chlorinated isocyanuric acids, and N,N-dichloro-p-toluenesulfonamide and the like. The preferred halogenating agents are chlorine, bromine, and sulfuryl chloride.

Suitable conditions for the reaction include those in which free halogen radicals are generated. For example, in the practice of the process of the invention, temperatures in the range of from about −40° centigrade to 200° centigrade, preferably 20° centigrade to 170° centigrade, are employed, also free radical chain initiators are desirably present, including actinic light, diacyl peroxides such as benzoyl peroxide, acetyl peroxide, alkyl or arylalkyl peroxides and hydroperoxides such as cumene hydroperoxide and acetone peroxide, peracids such as perbenzoic acid, m-chloroperbenzoic acid, perphthalic acid, and peracetic acid and azo compounds such as azobis-isobutyronitrile. These agents may be used separately or together. Generally, such catalysts are used at 0.001 percent to 5 percent concentration. Further adjuvants may be used to suppress ring chlorination, although the process of the invention does not require them. In general, these suppressing agents are believed to act by complexing with, and thus deactivating, traces of Lewis acids, such as ferric chloride, which would otherwise catalyze ring substitution; however, applicants do not wish to be bound by this theory. Such adjuvants include phosphorus chlorides, organic phosphates or phosphites such as triphenyl phosphate or phosphite, amides such as urea, acetamide and benzamide, and polyols such as glycerol, sorbitol and mannitol. The halogenation may conveniently be effected without a solvent, although halogen resistant solvents such as carbon tetrachloride and chlorobenzenes may be used if desired. Atmospheric pressure is conveniently employed, but sub- or super-atmospheric pressures are also operable. While the stoichiometry of the process calls for molar equivalents of halogenating agent, a moderate deficiency or excess may be employed, and the desired product may be separated from lower and higher halogenated products by distillation, crystallization, or other means.

That the halogenation process of the invention succeeds is especially surprising in view of the usual reactivity of the phenyl ring when it bears an oxygen atom. Unpredictably, it seems that placing a —COCl group on the phenolic hydroxyl group has so deactivated the ring toward halogen substitution or addition as to permit side chain halogenation.

Another process for preparing the haloformate compounds of the invention where the mentioned haloalkyl side chains are o- and/or p-halomethyl is by the reaction of phenyl haloformate having at least one unsubstituted position o- or p- to the —OCOX group with a haloalkylating agent such as formaldehyde (for a formaldehyde donor) plus hydrogen halide in the presence of a haloalkylating catalyst such as a Lewis acid catalyst. That this reaction is feasible is surprising in three respects: (1) firstly, the halomethylation of phenols has generally not been successful, except where the ring was substituted by bulky or electronegative substituents; (2) secondly, the carbonyl group present in the haloformate side chain would be expected to be deactivating to a Lewis acid catalyst, by complexing therewith and (3) thirdly, assuming the Lewis acid catalyst could be made to function, the —OCOX group would be expected to participate in the reaction (this group being known to acylate aromatic rings under Friedel-Crafts reaction condition) resulting in polymer formation. Surprisingly, the halomethylation of phenyl haloformates is found to proceed smoothly and under mild conditions.

The formaldehyde may be used as anhydrous monomer, trimer or polymer, or in the form of its reaction products with hydrogen halide, and/or CH₃OH, namely, halomethyl methyl ether or bis(chloromethyl) ether. In the case of these ethers, no additional hydrogen halide is required, although further hydrogen halide helps to produce improved yields. Suitable chloromethylating catalysts include Lewis acids, such as zinc chloride, boron trichloride, boron trifluoride, antimony chlorides, aluminum chloride, ferric chloride, tin tetrachloride, titanium chloride and other Lewis acid metal chlorides. Co-catalysts such as thionyl chloride are also helpful in some cases. Amounts from about 0.1 percent up to two molar equivalents of catalysts are used, the lower amounts where the ring is more reactive, (such as where it bears several alkyl groups), the larger amounts where the ring is less reactive (such as where it bears halogen substituents). The quantity will also depend on the strength of the catalyst chosen ($ZnCl_2$, $SnCl_4$, $SbCl_5$, relatively most active) and the temperature chosen (less catalyst needed at higher temperature).

The chloromethylation is conducted preferably in the liquid phase at $-60°$ to $+150°$. No solvent is required, but inert solvents may be used. Suitable solvents include aliphatic hydrocarbons, ethylene dichloride, methylene chloride, chloroform, benzene, dichlorobenzenes, nitromethane, other nitroalkanes, ethyl ether, and any others which are resistant to the reactants and catalyst. Other lower aldehydes such as acetaldehyde, propionaldehyde, and the like may be substituted for the formaldehyde to obtain the corresponding 1-chloroalkyl side chains on the phenyl ring. Likewise, hydrogen bromide may be substituted for hydrogen chloride, thus obtaining bromomethyl groups in the product.

The carbamate compounds of the invention may be prepared by reacting the novel haloformates of the present invention of the formula:

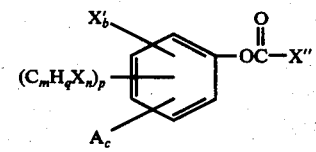

where X, X', A, m, n, p, q, b, and c are as defined above, and X" is a halogen chosen from bromine and chlorine, with an amine of the formula HNZZ' where Z and Z' are as above defined. It is surprising and unexpected that the reaction proceeds with the clean-cut selective replacement of X" rather than of both X and X", particularly since the chloroformate group is relatively sluggish in regard to chloride displacement compared to ordinary acid chloride. It is preferred that the reaction be conducted in the liquid phase at $-60°$ to $+170°$ centigrade, preferably $-40°$ to $+150°$, using an acceptor of HCl which may be one extra molar equivalent of HNZZ' or another base such as trialkylamine, pyridine, other tertiary amine, sodium carbonate, aqueous caustic soda or potash, or the like. While a solvent is not necessary, it is convenient to employ a solvent, for example, an aliphatic hydrocarbon, such as benzene, toluene, mineral spirits, hexane, and the like, a chlorocarbon such as ethylene dichloride, chlorobenzene, perchloroethylene, and the like, an ether such as ethyl ether, dioxane, tetrahydrofuran, anisole, and the like, a nitrohydrocarbon such as nitrobenzene and the like, a ketone, such as acetone, methyl ethyl ketone, and the like, or another solvent, such as acetonitrile, dimethylformamide, and others. It has also been found that water may conveniently be employed where the HNZZ' component is water soluble; generally, the haloformate reactant is not water soluble and a two-phase reaction mixture results, in which the haloformate reacts with the HNZZ' rather than undergoing hydrolysis.

When water is used as solvent for the HNZZ' reactant, one of the other solvents such as those named above may be used as solvent for the haloformate. The HCl acceptor may be conveniently chosen to be a water-soluble one such as caustic soda or potash, which have the advantage of low cost. These reactions are very rapid, and are generally complete in from 1 minute to one day; the limiting factor in the rapidity with which they can be run is often the rate at which the heat of reaction can be removed to hold the temperature at the desired level.

The product may be isolated by filtration or by distilling off of the solvent. Generally, the by product salt of the HCl acceptor can be filtered off or washed out with water.

The novel carbonates of the invention are represented by the formula:

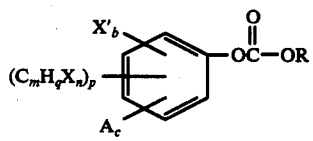

wherein the substituent R is selected from the group consisting of alkyl, preferably of one to six carbon atoms, and halo-substituted alkyl, such as chloro-substituted alkyl or bromo-substituted alkyl, and the remaining substituents:

X and X' are halogens of atomic weight between 34 and 81;

m is from 1 to 20;

q is equal to the remaining number of valences on the radical $C_mH_qX_n$;

n is from 1 to $2_{m+1}$;

p is from 1 to 5;

A is an alkyl radical, preferably of from 1 to about 6 carbon atoms;

c is from 0 to $(5-p-b)$, inclusive; and b is from 0 to $(5-p)$, inclusive.

In order that those skilled in the art may better understand the present invention, the manner in which it may be practiced, the following specific examples are given.

In the specification, examples and claims, all parts given are parts by weight and all temperatures are in degrees centigrade, unless otherwise specified.

EXAMPLE 1

α-Chloro-o-cresyl Chloroformate

To 100 parts of o-cresyl chloroformate, 1.4 parts of phosphorus trichloride and 0.1 part of benzamide, stirred at 118° to 120° centigrade and exposed to the radiation from a mercury vapor lamp, is added a solution of 0.8 part of benzoyl peroxide in 80 parts of sulfuryl chloride. The addition is carried out over 1.2 hours. The reaction mixture is then fractionally distilled to obtain 42 parts of a foreshot consisting principally of unreacted o-cresyl chloroformate and a main fraction of 63 parts of colorless liquid boiling at 60° to 65° centigrade, at 0.1 millimeter pressure absolute. The infrared spectrum of the material made, α-chloro-o-cresyl chloroformate, exhibited a band at 5.60 microns, indicating an acid chloride carbonyl.

Analysis: Calculated for $C_8H_6O_2Cl_2$: Cl (total) 34.6; Cl (hydrolyzable by KOH/alcohol) 34.6. Found: Cl (total) 34.7; Cl (hydrolyzable by KOH/alcohol) 34.7.

EXAMPLE 2

α,α-Dichloro-o-cresyl Chloroformate

To a stirred mixture of 70 parts of o-cresyl chloroformate and 1.4 parts of phosphorus trichloride was added 0.5 part of benzoyl peroxide in 112 parts of sulfuryl chloride at 118° to 125° centigrade over a priod of 3 hours. Then, when the reaction evolving HCl and $SO_2$ had subsided, the reaction vessel was illuminated by a mercury vapor lamp and a further 83.4 parts of sulfuryl chloride were added. The reaction mixture was found to have increased in weight by 23 parts, (theory, 24 parts for dichlorination). The product was then distilled to obtain the desired α,α-dichloro-o-cresyl chloroformate as a colorless liquid boiling at 84° to 86° (0.1 millimeter) and having the correct total and hydrolyzable chlorine content.

EXAMPLE 3

α,α-Dibromo-o-cresyl Bromoformate

In the same manner as Example 2, o-cresyl bromoformate and elemental bromine, employed in the place of o-cresyl chloroformate and sulfuryl chloride, result in α,α-dibromo-o-cresyl bromoformate.

EXAMPLE 4

α,α,α-Trichloro-o-cresyl Chloroformate

Chlorine gas was passed into a mixture of 50 parts of o-cresyl chloroformate, 1.2 parts of phosphorus trichloride, 0.2 part of benzamide, and 0.5 part of benzoyl peroxide at 130° to 140°, until no further hydrogen chloride evolution was observed. The product was then distilled to obtain 48 parts of colorless oil boiling at 82 to 92 degrees centigrade (0.08 millimeter). The infrared spectrum showed bands characteristic of ortho-disubstitution, indicating that none of the chlorine had attached to the benzene ring.

Analysis: Calculated for $C_8H_4O_2Cl_4$: Cl 57.5; Found: Cl 57.3.

Preparation of an N-methylcarbamate derivative (described hereinafter) yielded a crystalline product $C_9H_3O_2NCl_5$ the chlorine content of which was entirely hydrolyzable by KOH in refluxing ethanol.

EXAMPLES 5 – 19

The following examples were conducted according to the methods of Examples 1 – 4 above. In each case, a slight (5–20 percent) excess of halogenating agent was used relative to the number of halogen atoms to be introduced. The products were isolated by distillation and in most instances under vacuum, the boiling points of the products being listed below.

| Example No. | Haloformate Reactant (wt.) | Chlorinating Agent | Temp. °C | Time (Hrs.) | Product | Boiling Point °C | Analysis % Chlorine Calculated | % Chlorine Found[a] | % Chlorine Found[b] |
|---|---|---|---|---|---|---|---|---|---|
| 5 | m-cresyl chloroformate | $SO_2Cl_2$ | 135–140 | 5 | α-chloro-m-cresyl chloroformate | 79–81.5 (0.1 mm.) | 34.6 | 34.7 | 34.7 |
| 6 | m-cresyl chloroformate | $SO_2Cl_2$ | 138–140 | 6 | α,α-dichloro-m-cresyl chloroformate | 103–108 (0.25 mm.) | 44.5 | 44.4 | 43.1 |
| 7 | p-cresyl chloroformate | $SO_2Cl_2$ | 135–142 | 5 | α-chloro-p-cresyl chloroformate | 76–82 (0.1 mm) m.p.61-2° (recryst. from heptane) | 34.6 | 34.6 | 34.6 |
| 8 | p-cresyl chloroformate | $SO_2Cl_2$ | 135–145 | 7 | α,α-dichloro-p-cresyl chloroformate | 85–86 (0.1 mm.) | 44.5 | 43.3 | — |
| 9 | p-cresyl chloroformate | $SO_2Cl_2$ | 130–140 | 8¼ | α,α,α-trichloro-p-cresyl chloroformate | 92–94 (0.04 mm.) m.p. 48–49.5° | 51.8 | 50.8 | 50.8 |
| 10 | 3,5-xylenyl chloroformate | $SO_2Cl_2$ | 138–140 | 4 | α-chloro-3,5-xylenyl chloroformate | 84–89 (0.1 mm.) | 32.5 | 33.3 | 32.4 |
| 11 | 3,5-xylenyl chloroformate | $SO_2Cl_2$ | 138–140 | 9 | α,α'-dichloro-3,5-xylenyl chloroformate | 105–110 (0.09 mm.) | 42.0 | 40.7 | 40.8 |
| 12 | 3,5-xylenyl chloroformate | $SO_2Cl_2$ | 138–140 | 12 | α,α,α'-trichloro-3,5-xylenyl chloroformate | 134–136 (0.15 mm.) | 49.3 | 49.6 | 49.6 |
| 13 | 3,5-xylenyl chloroformate | $SO_2Cl_2$ | 136–140 | 16 | α,α,α,α'-tetrachloro-3,5-xylenyl chloroformate | 138.5–140 (0.05 mm.) | 55.1 | 55.4 | 55.2 |
| 14 | 2,3-xylenyl chloroformate | $SO_2Cl_2$ | 130–180 | 5 | α-chloro-2,3-xylenyl chloroformate | 90–95 (0.15 mm.) | 32.4 | — | 32.0 |
| 15 | 2,3-xylenyl chloroformate | $SO_2Cl_2$ | 130–180 | 10 | α,α'-dichloro-2,3-xylenyl chloroformate | 105–110 (0.1 mm.) | 42.0 | — | 41.3 |
| 16 | 3,4-xylenyl chloroformate | $SO_2Cl_2$ | 130–180 | 5 | α-chloro-3,4-xylenyl chloroformate | 90–95 (0.05 mm.) | 32.4 | — | 32.0 |
| 17 | 3,4-xylenyl chloroformate | $SO_2Cl_2$ | 130–180 | 10 | α,α'-dichloro 3,4-xylenyl chloroformate | 121–125 (0.15 mm.) | 42.0 | — | 41.9 |
| 18 | 3,5-diisopropyl phenyl chloroformate | $Cl_2$ | 145–150 | ½ | α-chloro-3,5-diisopropylphenyl chloroformate | 81–82 (0.025 mm.) | 22.9 | — | 22.8 |
| 19 | 2-allylphenyl chloroformate | $Cl_2$ | −20° (first 2 Cl), then 30–140° | ½ | 2-(2,3-dichloropropyl) phenyl chloroformate, and 2-(1,2,3-trichlorpropyl) phenyl | 115–117 (0.08 mm.) 126–130 (0.1–0.2 mm.) | 39.8 46.8 | 39.8 46.1 | — — |

| Example No. | Haloformate Reactant (wt.) | Chlorinating Agent | Temp. °C | Time (Hrs.) | Product | Boiling Point °C | % Chlorine Calculated | % Chlorine Found[a] | % Chlorine Found[b] |
|---|---|---|---|---|---|---|---|---|---|
| | | | | | chloroformate[c] | | | | |

[a] total
[b] hydrolyzable by KOH/alc.
[c] I.R. shows o-disubstitution pattern and absence of aliphatic C=C bond.

In a manner similar to Examples 5 to 19 the corresponding bromo analogs are prepared by utilizing bromine in the place of chlorine gas or $SO_2Cl_2$.

EXAMPLE 20

Preparation of α,4-Dichloro-o-cresyl Chloroformate

To 13 parts of 4-chloro-o-cresyl chloroformate were slowly added 13.5 parts of sulfuryl chloride under illumination by a mercury vapor lamp at 130° – 140° over 2 hours. The product was then distilled to obtain 9 parts of colorless liquid, boiling point 82°-86°(0.15 millimeter).

Analysis: Calculated for $C_8H_5O_2Cl_3$: Cl (hydrolyzable by KOH/alcohol) 29.6; Found: Cl (hydrolyzable by KOH/alcohol) 30.3.

In a similar manner, α,3,4,6-tetrachloro-o-cresyl chloroformate and α, α,3,4,6-pentachloro-o-cresyl chloroformate were prepared by chlorination of 3,4,6-trichloro-o-cresyl chloroformate at 135-175. Similarly, α, α, α',α';2,4-hexachloro-3,5-xylenyl chloroformate was prepared by chlorination of 2,4-dichloro-3,5-xylenyl chloroformate.

EXAMPLE 21

Chlorination of o-Cresyl Chloroformate in Absence of Catalysts and Inhibitors

To 50 parts of o-cresyl chloroformate at 80° were added several parts of sulfuryl chloride. No hydrogen chloride evolution was noted. The temperature was raised to 115° causing evolution of hydrogen chloride. At 115°-118°, the gradual addition of sulfuryl chloride was continued, until after 11 hours, a total of 44.4 parts of sulfuryl chloride was added. The product was then freed of volatile materials by briefly applying vacuum, e.g., for 1 to 5 minutes. The residual chloroformate product was a liquid containing both ring and side chain monochlorinated o-cresyl chloroformate.

Analysis: Calculated for α-chloro-o-cresyl chloroformate: Cl (total) 34.6; Cl (hydrolyzable by KOH/alcohol) 34.6. Calculated for ring-chloro-o-cresyl chloroformate: Cl (total) 34.6; Cl (hydrolyzable by KOH/alcohol) 17.3. Found: Cl (total) 32.6; Cl (hydrolyzable by KOH/alcohol) 26.8.

EXAMPLE 22

Chloromethylation of Phenyl Chloroformate

Into a stirred mixture of 156 parts of phenyl chloroformate, 39 parts of paraformaldehyde, 50 parts of powdered zinc chloride, and 500 parts of chloroform, was passed anhydrous chloride at 55°-60° for 8 hours. Then, the reaction mixture was added to ice water, stirred and the organic layer taken off and dried over magnesium sulfate. It was then filtered, the solvent was evaporated, and the residual liquid was distilled to obtain 40 parts of product, boiling point 84°-92° (0.1 millimeter). The colorless distillate crystallized on standing and was recrystallized from a benzeneheptane mixture to obtain colorless crystals, melting point 60°-61.5°. This was found by infrared comparison to be the same compound as produced by α-monochlorination of p-cresyl chloroformate.

Analysis: Calculated for $C_8H_6O_2Cl_2$: Cl (total) 34.6; Cl (hydrolyzable by KOH/alcohol) 34.5.

The bulk of the other material collected in the above distillation consisted of lower-boiling unreacted phenyl chloroformate, which was recycled to the next chloromethylation batch.

EXAMPLE 23

Chloromethylation of 3,5-Xylenyl Chloroformate

Into a stirred mixture of 37 parts of 3,5-xylenyl chloroformate, 78 parts of paraformaldehyde, 10 parts of powdered anhydrous zinc chloride, and 150 parts of chloroform at 20-30 degrees, was passed hydrogen chloride gas over 10½ hours. The paraformaldehyde slowly dissolved. Then the reaction mixture was agitated briefly with ice water, after which the organic layer was decanted, dried over magnesium sulfate, filtered, and solvent was evaporated off. The residual liquid was distilled to obtain 17 parts of chloromethyl-3,5-dimethylphenyl chloroformate, boiling point 80° – 85° (0.005 millimeter), in which the position of the chloromethyl group is indicated to be mostly para by NMR analysis.

Analysis: Calculated for $C_{10}H_{10}O_2Cl_2$: Cl 30.4. Found: Cl 30.2.

In the same manner, p-cresyl chloroformate is chloromethylated to produce 2-(chloromethyl)-p-cresyl chloroformate, 2,3,5,6-tetramethylphenyl chloroformate is chloromethylated to produce 4-chloromethyl-2,3,5,6-tetramethylphenyl chloroformate, and 2-cyclopentylphenyl chloroformate is chloromethylated to produce 4-chloromethyl-2-cyclopentylphenyl chloroformate.

The haloalkylphenyl chloroformates of the invention exhibit pesticidal activity per se, especially as nematocides, fungicides, and herbicides.

EXAMPLE 24

Nematocidal Activity

Into soil heavily infested with *Melodogyne incognita*, var. acrita, a plant pathogenic nematode species which causes "root knot disease" of various crops, was incorporated α-chloro-2,3-xylenyl chloroformate at the rate of 147 pounds per acre. After a two-week waiting period, tomato seedlings were planted therein. Tomatoes were also planted in an adjacent unfumigated infested area. One month later, the plants in the treated area were found to be substantially free of root knots, whereas the plants in the untreated area were heavily damaged by root knots caused by nematode attack.

Similar results were obtained with α-bromo-2,3-xylenyl chloroformate.

EXAMPLE 25

Herbicidal Activity

A heavy stand of roadside weeds (goldenrod and wild carrot, principally) was sprayed with a solution of α,α,α',α',2,4-hexachloro-3,5-xylenyl chloroformate (4 pounds) in kerosene (40 gallons). When examined one day later and three weeks later, substantially 100 percent kill was observed, whereas with the kerosene along only a transitory foliage burn followed by regrowth occurred.

The novel compounds of the invention are useful also as polymer intermediates for preparation of polyethers and polyether-poly carbonates.

EXAMPLE 26

Conversion of α-Chloro-o-cresyl Chloroformate to Polycarbonate Resin

A 10 percent solution of α-chloro-o-cresyl chloroformate in hexane and a 10 percent aqueous solution of sodium hydroxide were agitated vigorously, together at 20° centigrade. In 15 minutes, a thick precipitate of polymer had formed. After 30 minutes, the mixture had filtered and the solids washed with water and hexane. Upon drying the solids, there was obtained a white solid polymer, insoluble in methanol, soluble in tetrahydrofuran. A film cast from tetrahydrofuran was clear, water-white and non-tacky. The infrared spectrum shows a strong band at 5.6 microns, characteristic of the —O—OO—O— linkage. The structure of the polymer is believed to have carbonate and other linkages in the chain, with terminal —CH$_2$Cl groups capable of further reaction with nucleophiles. The molecular weight of this product is increased by further reacting with disodium bisphenol-A, preferably in a co-solvent such as dioxane.

EXAMPLE 27

Preparation of Polycarbonate-Polyether Resin

A mixture of one mole of α-chloro-p-cresyl chloroformate, one mole of the disodium salt of bisphenol-A, and 2,800 cc. of p-dioxane was stirred and the temperature of the reaction mixture was gradually raised to 100° until titration of an aliquot showed that all of the chlorine has been released as sodium chloride. Then, the solution was filtered to remove salt and was concentrated under vacuum, and it was added to a stirred mixture of 2,000 cc. of water and 2,000 cc. of benzene. The benzene layer was then separated and evaporated to obtain the desired product as a resin, capable of forming transparent films. The infrared spectrum showed the presence of carbonate linkages (band at 5.6 microns) and ether linkages.

The resultant resin is useful as the film-forming component of electrically insulating coatings.

Analogous resins are produced by substitution of α-chloro-m- or -o-cresyl chloroformate for the p-isomer in the above procedure. Analogous resins prepared by use of ring polychlorinated or ring-brominated α-chloro-o- m-, or p-cresyl chloroformates are self-extinguishing when ignited.

The haloformate compounds of the invention are useful as intermediates for preparation of new aryl esters, many of which exhibit perticidal properties to a high degree.

EXAMPLE 28

Preparation of α-Chloro-o-cresyl N-Methylcarbamate

To 25 parts of α-chloro-o-cresyl chloroformate (Example 1) in 40 parts of hexane was added 12.4 parts of methylamine in 100 parts of aqueous solution at 5°–10° with stirring. After 15 minutes, the precipitated solid was filtered out, washed with water, dried in air and recrystallized from benzene-heptane mixture to obtain 20 parts of colorless crystalline solid, melting point 89°–90° centigrade. The infrared spectrum showed the characteristic NH band at 3 microns and the carbamate carbonyl band at 5.8 microns.

Analysis: Calculated for C$_9$H$_{10}$O$_2$NCl: Cl 17.8, N 7.0. Found: Cl 17.6, N 7.0.

EXAMPLE 29

Preparation of α-Bromo-o-cresyl-N-methylcarbamate

The corresponding bromine compound was prepared by utilizing α-bromo-o-cresyl bromoformate in place of the α-chloro-o-cresyl chloroformate.

EXAMPLES 30 – 75

In a similar fashion, various of the side chain chlorinated alkylphenyl-chloroformates of the invention were caused to react with various amines to obtain novel (haloalkyl)phenyl carbamates, as shown in the following Table.

| Ex. No. | Haloformate Reactant | Amine Reactant | Product | Physical Properties | Empirical Formula | Cl Calculated | Cl Found[1] | N Calculated | N Found |
|---|---|---|---|---|---|---|---|---|---|
| 30 | α-chloro-o-cresyl chloroformate | NH$_3$ | α-chloro-o-cresyl carbamate | colorless crystals m.p. 119–120° C | C$_8$H$_8$C$_2$NCl | — | — | 7.5 | 7.2 |
| 31 | α,α-dichloro-o-cresyl chloroformate | CH$_3$NH$_2$ | α,α-dichloro-o-cresyl N-methylcarbamate | colorless crystals 108–m.p. 110° C | C$_9$H$_9$O$_2$NCl$_2$ | 30.3 | 29.4 | 5.98 | 5.94 |
| 32 | α-chloro-m-cresyl chloroformate | CH$_3$NH$_2$ | α-chloro-m-cresyl N-methylcarbamate | colorless crystals m.p. 84.5–85° C | C$_9$H$_{10}$O$_2$NCl | — | — | 7.0 | 6.7 |
| 33 | α,α-dichloro-m-cresyl chloroformate | CH$_3$NH$_2$ | α,α-dichloro-m-cresyl N-methylcarbamate | syrup (undistillable) | C$_9$H$_9$O$_2$NCl$_2$ | 30.3 | 28.7 | 5.98 | 5.68 |
| 34 | α-chloro-p-cresyl chloroformate | CH$_3$NH$_2$ | α-chloro-p-cresyl N-methylcarbamate | colorless crystals m.p. 131–3° C | C$_9$H$_{10}$O$_2$NCl | — | — | 7.0 | 6.7 |
| 35 | α,α-dichloro-p-cresyl chloroformate | CH$_3$NH$_2$ | α,α-dichloro-p-cresyl N-methylcarbamate | colorless crystals m.p. 95.5– | C$_9$H$_9$O$_2$NCl$_2$ | — | — | 5.98 | 5.70 |

-continued

| Ex. No. | Haloformate Reactant | Amine Reactant | Product | Physical Properties | Empirical Formula | Cl Calculated | Cl Found[1] | N Calculated | N Found |
|---|---|---|---|---|---|---|---|---|---|
| 36 | α-chloro-3,5-xylenyl chloroformate | $CH_3NH_2$ | α-chloro-3,5-xylenyl chloroformate | 97° C colorless crystals m.p. 95-95.5° C | $C_{10}H_{12}O_2NCl$ | 16.6 | 17.3 | 6.56 | 6.96 |
| 37 | α,α'-dichloro-3,5-xylenyl chloroformate | $CH_3NH_2$ | α,α'-dichloro-3,5-xylenyl N-methylcarbamate | colorless crystals m.p. 120-122° C | $C_{10}H_{11}O_2NCl_2$ | 28.6 | 28.0 | 5.64 | 5.40 |
| 38 | α,α,α'-trichloro-3,5-xylenyl chloroformate | $CH_3NH_2$ | α,α,α'-trichloro-3,5-xylenyl N-methylcarbamate | colorless crystals m.p. 81.5-83° C | $C_{10}H_{10}O_2NCl_3$ | — | — | 4.96 | 4.90 |
| 39 | α,α',α'-tetrachloro-3,5-xylenyl chloroformate | $CH_3NH_2$ | α,α,α,α'-tetrachloro-3,5-xylenyl N-methylcarbamate | colorless crystals m.p. 110-113° C | $C_{10}H_9O_2NCl_4$ | 44.6 | 44.0 | 4.43 | 4.26 |
| 40 | α-chloro-3,5-diisopropylphenyl chloroformate | $CH_3NH_2$ | α-chloro-3,5-diisopropylphenyl N-methylcarbamate | undistillable tan syrup | $C_{14}H_{20}O_2NCl$ | — | — | 5.20 | 4.5 |
| 41 | α,α'-dichloro-3,4-xylenyl chloroformate | n-butylamine | α,α'-dichloro-3,4-xylenyl N-n-butylcarbamate | syrup | $C_{13}H_{17}O_2NCl_2$ | — | — | 4.83 | 4.90 |
| 42 | " | $(CH_3)_2CHNH_2$ | α,α'-dichloro-3,4-xylenyl N-isopropylcarbamate | syrup | $C_{12}H_{15}O_2NCl_2$ | — | — | 5.07 | 5.2 |
| 43 | " | Morpholine | α,α'-dichloro-3,4-xylenyl morpholine-1-carboxylate | syrup | $C_{13}H_{15}O_3NCl_2$ | — | — | 4.60 | 4.8 |
| 44 | " | Cyclohexylamine | α,α'-dichloro-3,4-xylenyl N-cyclohexyl carbamate | m.p. 108-9° | $C_{15}H_{19}O_2NCl_2$ | — | — | 4.52 | 4.9 |
| 45 | " | Aziridine (+Et$_3$N) | α,α'-dichloro-3,4-xylenyl aziridine-1-carboxylate | syrup | $C_{11}H_{11}O_2NCl_2$ | — | — | 5.38 | 5.3 |
| 46 | α,α'-dichloro-2,3-xylenyl chloroformate | $NH_3$ | α,α'-dichloro-2,3-xylenyl carbamate | m.p. 126-8° | $C_9H_9O_2NCl_2$ | — | — | 5.98 | 5.6 |
| 47 | " | Cyclohexylamine | α,α'-dichloro-2,3-xylenyl N-cyclohexylcarbamate | m.p. 116-8° | $C_{15}H_{19}O_2NCl_2$ | — | — | 4.52 | 4.1 |
| 48 | " | Aziridine (+Et$_3$N) | α,α'-dichloro-2,3-xylenyl aziridine-1-carboxylate | solid, decomposes on heating | $C_{11}H_{11}O_2NCl_2$ | — | — | 5.38 | 5.2 |
| 49 | α,α'-dichloro-3,5-xylenyl chloroformate | $NH_3$ | α,α'-dichloro-3,5-xylenyl carbamate | m.p. 134-6° | $C_9H_9O_2NCl_2$ | 30.3 | 29.4 | 5.98 | 5.3 |
| 50 | " | $(CH_3)_2CHNH_2$ | α,α'-dichloro-3,5-xylenyl N-isopropylcarbamate | m.p. 81-3° | $C_{12}H_{15}O_2NCl_2$ | 25.7 | 24.9 | 5.07 | 4.8 |
| 51 | " | Cyclohexylamine | α,α'-dichloro-3,5-xylenyl N-cyclohexylcarbamate | m.p. 103-5° | $C_{15}H_{19}O_2NCl_2$ | 22.9 | 22.0 | 4.52 | 4.4 |
| 52 | " | Di-n-butylamine | α,α'-dichloro-3,5-xylenyl N,N-di-n-butylcarbamate | syrup | $C_{17}H_{21}O_2NCl_2$ | 20.8 | 21.0 | 4.09 | 3.8 |
| 53 | " | Aziridine (No Et$_3$N) | α,α'-dichloro-3,5-xylenyl N-(2-chloroethyl)carbamate | solid, decomposes on heating | $C_{11}H_{12}O_2NCl_3$ | 36.4 | 36.0 | — | — |
| 54 | " | Morpholine | α,α'-dichloro-3,5-xylenyl Morpholine-1-carboxylate | syrup | $C_{13}H_{15}O_3Cl_2N$ | 23.3 | 22.5 | 4.60 | 4.34 |
| 55 | α-chloro-o-cresyl chloroformate | aniline | α-chloro-o-cresyl N-phenylcarbamate | m.p. 94-6° C | $C_{14}H_{12}ClNO_2$ | 13.6 | 13.1 | 5.37 | 5.37 |
| 56 | α-chloro-o-cresyl chloroformate | m-chloroaniline | α-chloro-o-cresyl N-m-chlorophenyl carbamate | m.p. 84-86° C | $C_{14}H_{11}Cl_2NO_2$ | 24.0 | 23.9 | 4.72 | 4.64 |
| 57 | α-chloro-o-cresyl chloroformate | p-chloroaniline | α-chloro-o-cresyl N-p-chlorophenyl carbamate | m.p. 113-15° | $C_{14}H_{11}Cl_2NO_2$ | 24.0 | 23.9 | 4.72 | 4.59 |
| 58 | α-chloro-o-cresyl chloroformate | 3,4-dichloroaniline | α-chloro-o-cresyl N-3,4-dichlorophenylcarbamate | m.p. 109-111° C | $C_{14}H_{10}Cl_3NO_2$ | 32.3 | 32.0 | 4.24 | 4.02 |
| 59 | α-chloro-o-cresyl chloroformate | dimethyl amine | α-chloro-o-cresyl N,N-dimethylcarbamate | oil | $C_{10}H_{12}ClNO_2$ | 16.6 | 16.3 | 6.57 | 6.48 |
| 60 | α-chloro-m-cresyl chloroformate | aniline | α-chloro-m-cresyl N-phenylcarbamate | m.p. 123-6° C | $C_{14}H_{12}ClNO_2$ | 13.6 | 13.9 | 5.37 | 5.29 |
| 61 | α-chloro-m-cresyl chloroformate | m-chloroaniline | α-chloro-m-cresyl N-m-chlorophenyl carbamate | m.p. 70-71.5° C | $C_{14}H_{11}Cl_2NO_2$ | 24.0 | 23.9 | 4.72 | 4.63 |
| 62 | α-chloro-m-cresyl chloroformate | p-chloroaniline | α-chloro-m-cresyl N-p-chlorophenylcarbamate | m.p. 132-3° C | $C_{14}H_{11}Cl_2NO_2$ | 24.0 | 23.8 | 4.72 | 4.48 |

-continued

| Ex. No. | Haloformate Reactant | Amine Reactant | Product | Physical Properties | Empirical Formula | Cl Calculated | Cl Found[1] | N Calculated | N Found |
|---|---|---|---|---|---|---|---|---|---|
| 63 | α-chloro-m-cresyl chloroformate | 3,4-dichloroaniline | α-chloro-m-cresyl N-3,4-dichlorophenyl carbamate | m.p. 110-111° C | $C_{14}H_{10}Cl_3NO_2$ | 32.3 | 31.7 | 4.24 | 3.98 |
| 64 | α-chloro-m-cresyl chloroformate | dimethylamine | α-chloro-m-cresyl N,N-dimethylcarbamate | oil | $C_{10}H_{12}ClNO_2$ | 16.6 | 16.2 | 6.57 | 5.73 |
| 65 | α-chloro-p-cresyl chloroformate | aniline | α-chloro-p-cresyl N-phenyl carbamate | m.p. 132-3 | $C_{14}H_{12}ClNO_2$ | 13.6 | 13.2 | 5.37 | 5.22 |
| 66 | α-chloro-p-cresyl chloroformate | m-chloroaniline | α-chloro-p-cresyl N-m-chlorophenyl carbamate | m.p. 113-4° C | $C_{14}H_{11}Cl_2NO_2$ | 24.0 | 23.7 | 4.72 | 4.49 |
| 67 | α-chloro-p-cresyl chloroformate | p-chloroaniline | α-chloro-p-cresyl N-p-chlorophenyl carbamate | m.p. 156-9° C | $C_{14}H_{11}Cl_2NO_2$ | 24.0 | 22.5 | 4.72 | 4.71 |
| 68 | α-chloro-p-cresyl chloroformate | 3,4-dichloroaniline | α-chloro-p-cresyl N-3,4-dichlorophenylcarbamate | m.p. 115.5-117° | $C_{14}H_{10}Cl_3NO_2$ | 32.3 | 25.0 | 4.24 | 2.63 |
| 69 | α-chloro-p-cresyl chloroformate | dimethylamine | α-chloro-p-cresyl N,N-dimethyl carbamate | m.p. 68-69.5° C | $C_{10}H_{12}ClNO_2$ | 16.6 | 16.4 | 6.57 | 7.10 |
| 70 | 2-(2,3-dichloropropyl) phenyl chloroformate | $CH_3NH_2$ | 2-(2,3-dichloropropyl) phenyl N-methylcarbamate | syrup (undistillable) | $C_{11}H_{13}Cl_2NO_2$ | 27.1 | 29.0 | 5.35 | 4.74 |
| 71 | α-chloro-2,3-xylenyl chloroformate | $CH_3NH_2$ | α-chloro-2,3-xylenyl N-methyl carbamate | m.p. 72-84° (isomer mixture) | $C_{10}H_{12}O_2NCl$ | — | — | 6.65 | 7.0 |
| 72 | α,α'-dichloro-2,3-xylenyl chloroformate | $CH_3NH_2$ | α,α'-dichloro-2,3-xylenyl N-methylcarbamate | m.p. 138-9° | $C_{10}H_{11}O_2NCl$ | 28.6 | 28.6 | — | — |
| 73 | α-chloro-3,4-xylenyl chloroformate | $CH_3NH_2$ | α-chloro-3,4-xylenyl N-methylcarbamate | m.p. 83-6° | $C_{10}H_{12}O_2NCl$ | — | — | 6.55 | 6.3 |
| 74 | α,α'-dichloro-3,4-zylenyl chloroformate | $CH_3NH_2$ | α,α'-dichloro-3,4-xylenyl N-methylcarbamate | m.p. 115-7° | $C_{10}H_{11}O_2NCl$ | 28.6 | 28.5 | — | — |
| 75 | Chloromethyl-3,5-xylenyl chloroformate | $CH_3NH_2$ | Chloromethyl-3,5-xylenyl N-methyl carbamate | m.p. 78-110° (isomer mixture) | $C_{11}H_{14}O_2NCl$ | 15.6 | 16.2 | — | — |

[1] Hydrolyzable by KOH/alc.

The haloalkylphenyl carbamates derived from the haloalkylphenyl chloroformates of the invention are useful as pesticides. In particular, the N-unsubstituted, N-lower alkyl and N,N-di(lower alkyl) carbamates, and still more particularly the N-methyl and N,N-dimethyl-carbamates are insecticidal. Surprisingly, placing two halogen atoms on the side chain yields carbamates of enhanced insecticidal activity, whereas placing two halogen atoms on the benzene ring practially destroys such activity.

EXAMPLE 76

Bean plants infested with black bean aphids were sprayed with 0.1 percent aqueous dispersions of α-chloro-o-cresyl N-methylcarbamate, α,α-dichloro-m-cresyl N-methylcarbamate, and α,α-dichloro-o-cresyl N-methylcarbamate. After two days, 100 percent mortality of the aphids was observed in each case.

EXAMPLE 77

Third instar larvae of the Mexican bean beetle were placed on bean plants with 0.1 percent aqueous dispersions of α-chloro-3,5-xylenyl N-methylcarbamate, 2-(2,3-dichloropropyl) phenyl N-methylcarbamate, and 2-(1,2,3-trichloropropyl) phenyl N-methylcarbamate. After two days, 60 percent kill was observed with the first compound and 100 percent kill with the second and third compounds.

The carbamates derived from the haloalkylphenyl chloroformates of the invention are also useful as herbicides, especially the N-aryl, N-chloroalkyl, N-higher (alkyl), N,N-dialkyl, N-cycloalkyl, N,N-ethylene, (i.e., aziridinyl-1-carboxylates), and N,N-3-oxapentamethylene (i.e., morpholine1-carboxylates), as well as, in general, those carbamates having ring halogen in addition to side chain halogen, as shown in Example 97 below.

The α-haloalkylphenyl carbamates, carbonates and the parent phenols derived from the α-haloalkylphenyl haloformates of the invention also may be converted to further useful pesticides by nucleophilic displacement of the α-halogen which exhibits a high degree of reactivity. In this manner, the utility of the novel α-haloalkyl haloformates of the invention encompasses the use of these new compounds in an extremely broad range of useful conversions to valuable products, as shown in the following examples.

EXAMPLE 78

Preparation of α-(Diethoxyphosphinyl)-o-cresyl N-Methylcarbamate

A mixture of 1 part each of α-chloro-o-cresyl N-methylcarbamate and triethyl phosphite was heated at 100° for 9½ hours, during which time one molar equivalent of ethyl chloride was liberated. The reaction mixture was then evaporated at 100° under 0.25 mm. pressure to remove unreacted phosphite, leaving the desired phosphonate as a colorless clear syrup.

Anal. Calcd. for $C_{13}H_{20}O_5NP$: P, 10.3; N, 4.6; Cl, 0.0. Found: P, 9.64; N, 4.2; Cl, 0.1.

EXAMPLE 79

α-Dimethoxyphosphinyl-o-cresyl N-Methylcarbamate

The product, from α-chloro-cresyl N-methylcarbamate and excess trimethyl phosphite reacted at 100° as in the preceding example, is a light tan syrup.

Anal. Calcd. for $C_{11}H_{16}O_5NP$: P, 11.0; Found: P, 12.0 (undistilled crude).

By conducting the reaction at 140°, methyl isocyanate is lost and the free α-dimethyloxyphosphinyl-o-cresol is obtained.

In a similar manner to Examples 78 and 79 the same phosphonate compounds were prepared by utilizing the α-bromo-o-cresyl N-methylcarbamate in place of the α-chloro-o-cresyl N-methylcarbamate.

EXAMPLE 80

α-(Di-n-butoxyphosphinyl)-o-cresol and α-(Di-n-Butoxyphosphinyl)-o-cresyl N-methyl carbamate The initial product, made by heating 10 parts of α-chloro-o-cresyl N-methylcarbamate and 15 parts of tri-n-butyl phosphite at 130° - 135°, is a light tan oil which is found to have lost the N-methylcarbamate group and is established by infrared (OH band) and phosphorus analysis to be the free phenol, α-(di-n-butoxyphosphinyl)-o-cresol.

Anal. Calcd. for $C_{15}H_{25}O_4P$: P, 10.3; Found: P, 10.8.

To this phenol was added a molar excess of methyl isocyanate and a trace of dibutyl tin laurate catalyst. After standing 10 hours, the excess isocyanate was removed at 0.15 mm. vacuum leaving the desired N-methylcarbamate as a clear light tan oil having the correct nitrogen analysis.

In a like manner, the following are made:

α-dimethoxyphosphinyl-m-cresol and the corresponding N-methylcarbamate (from α-chloro-m-cresyl N-methylcarbamate and trimethyl phosphite), α-diethoxyphosphinyl-p-cresol and the corresponding N-methylcarbamate (from α-chloro-p-cresyl N-methylcarbamate and triethyl phosphite), α-dimethoxyphosphinyl-3,5-xylenol and the corresponding N-methylcarbamate (from α-chloro-3,5-xylenyl N-methylcarbamate and trimethyl phosphite), α,α-bis(diethoxyphosphinyl)-2,4-, 2,5-, 3,4- and 2,5-xylenol and the corresponding N-methylcarbamates (from α,α'-dichloro-2,4-, 3,5-, 3,4- and 2,5-xylenyl N-methylcarbamates and triethyl phosphite), α-di(heptadecyloxy)phosphinylpseudocumenol and the corresponding N-methylcarbamate (from α-chloropseudocumenyl N-methylcarbamate and methyl di(-heptadecyl)phosphite).

These side chain phosphonate-substituted phenols are useful as flame retardant co-monomers in phenolic resins. Furthermore, the carbamates derived from them have pesticidal properties.

EXAMPLE 81

Bean plants infested with black bean aphids were sprayed with 0.1 percent aqueous dispersions of α-(dimethoxyphosphinyl)-o-cresyl N-methylcarbamate, and α-(diethoxyphosphinyl)-o-cresyl N-methylcarbamate.

In 48 hours, 92 percent and 100 percent aphid mortality, respectively, was observed.

Further examples of nucleophilic displacements of α-haloalkylphenyl N-methylcarbamates derived from the haloformates of the invention include displacements by anions of the $RX^-$ type, where R is a hydrocarbyl or acyl group and X is oxygen or sulfur. These reactions are general for virtually any $RX^-$ nucleophile, and are illustrated by the following few examples. The products of these reactions show valuable pesticidal activity.

EXAMPLE 82

α-Acetoxy-o-cresyl N-Methylcarbamate

A mixture of 4.2 parts of sodium acetate and 10 parts of α-chloro-o-cresyl chloroformate in 75 parts of glacial acetic acid is heated at 100° for 2 days. The acetic acid was stripped under reduced pressure, the residue taken up in benzene, washed with water, and evaporated to 100° (0.1 mm) to obtain 8 parts of α-acetoxy-o-cresyl N-methylcarbamate, a pale yellow syrup. The infrared spectrum shows two overlapping bands in the carbonyl region, indicative of the ester and carbamate structures.

Anal. Calcd. for $C_{11}H_{13}O_4N$: N, 6.3; Found: N, 6.7.

In a similar manner are produced α-isobutyroxy-o-cresyl N-methylcarbamate (using sodium isobutyrate), α-benzoyloxy-o-cresyl N-methylcarbamate (using sodium benzoate). Analogously, α,α'-diacetoxy-3,5-xylenyl N-methylcarbamate is produced from α,α'-dichloro-3,5-xylenyl N-methylcarbamate and sodium acetate, and α-(2,4-dichlorophenoxyacetoxy)-2,3,4,5-tetrachloro-o-cresyl N,N-dimethylcarbamate is produced from α,2,3,4,5-pentachloro-o-cresyl N,N-dimethylcarbamate and sodium 2,4-dichlorophenoxyacetate.

EXAMPLE 83

α-(N,N-Dimethylthiocarbamylthio)-o-cresyl N-Methylcarbamate

A mixture of 10 parts of α-chloro-o-cresyl N-methylcarbamate and 18 parts of 40 percent aqueous sodium dimethyldithiocarbamate was stirred for 4½ hours at 30°. The precipitated solids were filtered out, washed with water, dried and recrystallized from benzene to obtain 11 parts of colorless crystals, m.p. 147°-148°.

Anal. Calcd. for $C_{12}H_{16}O_2S_2N_2$: N, 9.86; Found: N, 9.56.

This compound, sprayed at the rate of 125 parts per million in aqueous dispersion onto bean plants infested with larvae of Mexican bean beetle, produced 100 parts percent beetle mortality in 2 days.

EXAMPLE 84

α-(N,N-Diethylthiocarbamylthio)-o-cresyl N-methylcarbamate

The procedure of the preceding examples was followed, employing 16.6 parts of 51.4 percent aqueous sodium diethyldithiocarbamate. The product was a colorless crystalling solid, m.p. 59°-60° Centigrade.

Anal. Calcd. for $C_{14}H_{20}O_4N_2S_2$: N, 8.97; Found: N, 8.78.

In an analogous manner, α-chloro-o-cresyl N-methylcarbamate was converted to α-(N-methylthiocarbamylthio)-o-cresyl N-methylcarbamate (by reaction with sodium N-methyldithiocarbamate), to α-(N,N-dibutylthiocarbamylthio)-o-cresyl N-methylcarbamate (by reaction with sodium N,N-dibutyldithiocarbamate) and to α-(N,N-dipropylcarbamylthio)-o-cresyl N-methylcarbamate (by reaction with potassium N,N-dipropylthiolcarbamate). Likewise α-chloro-3,5-xylenyl N-methylcarbamate was converted to α-(N,N-diethylthiocarbamylthio)-3,5-xylenyl N-methylcarbamate (by reaction with sodium diethyldithiocarbamate). The thiocarbamate compounds thus produced are pesticidally active.

In addition to insecticidal activity, these compounds exhibit fungicidal, germicidal, and plant growth regulatory properties.

EXAMPLE 85

α-Thiocyano-o-cresyl N-methylcarbamate

A mixture of 10 parts of α-chloro-o-cresyl N-methylcarbamate and 4.05 parts of sodium thiocyanate in 200 parts of ethanol was stirred for 15 hours, filtered with clay and charcoal to remove salt, the solvent evaporated, and the residue recrystallized from carbon tetrachloride to obtain 4 parts of colorless crystals, m.p. 77°–78° Centigrade. The infrared spectrum established that the carbamate structure was present (NH at 3.03 microns, C=O at 5.85 microns) as well as the —SCN group (C=N at 4.68 microns).

Anal. Calcd. for $C_{10}H_{10}O_2N_2S$: N, 12.60; Found: N, 12.61.

This compound admixed with nematode-infested soil at 147 pounds per acre, substantially prevented nematode-caused root damage on cucumber seedlings planted in this soil. The same compound applied to soil at 64 pounds per acre killed aphids on bean seedlings planted in the treated soil, thus exhibiting systemic action.

In a similar manner, α-thiocyano-3,5-xylenyl N-methylcarbamate, a colorless solid, m.p. 90°–91°, was prepared from α-chloro-3,5-xylenyl N-methylcarbamate. Similarly, α,α'-dithiocyano-3,5-xylenyl N-methylcarbamate was made from α,α'-dichloro-3,5-xylenyl N-methylcarbamate and α,α'-dithiocyano-2,3-xylenyl N-methylcarbamate from the corresponding dichloro compound. Similarly, using sodium cyanide or cuprous cyanide in place of thiocyanate, the analogous α-cyano compounds were made. For example, α-cyano-o-cresyl N-methylcarbamate was prepared from α-chloro-o-cresyl N-methylcarbamate and CuCN.

By reaction of the α-haloalkylphenyl esters described above with nucleophiles of the RS− or RO− type where R is acyl or hydrocarbyl, a large number of valuable pesticides may be made.

EXAMPLE 86

α-(Diethoxythiophosphinylthio)-o-cresyl N-methylcarbamate

A mixture of 10 parts of α-chloro-o-cresyl N-methylcarbamate and 15 parts of sodium, O,O-diethylphosphorodithiolate in 80 parts of methyl ethyl ketone is held at 35°–50° Centigrade for 6 days. The solution is then washed with water and aqueous sodium bicarbonate, dried over magnesium sulfate, filtered and stripped to 100° (0.2 mm) leaving the product as 15.5 parts of pale tan syrup.

Anal. Calcd. for $C_{13}H_{20}O_4NS_2P$: N, 4.42; Found: N, 4.52.

This compound, sprayed at 0.1 percent in aqueous dispersion onto nasturtium infested with two-spotted mites, produced 100 percent mortality of mites in 24 hours, as well as ovicidal effects as shown by the failure of mites to hatch from eggs present at the time of spraying.

In an analogous manner are produced α-(dimethoxythiophosphinylthio)-3,5- and 3,4-xylenyl N-methylcarbamate from α-chloro-3,5- and α-chloro-3,4-xylenyl N-methylcarbamate and sodium O,O-dimethylphosphorodithiolate; similarly, α-(diisopropoxythiophosphinylthio)-o-cresyl N,N-dimethylcarbamate is prepared from α-chloro-o-cresyl N,N-dimethylcarbamate and sodium O,O diisopropylphosphorodithiolate.

EXAMPLE 87

α-Methoxy-o-cresyl N-methylcarbamate

To 10 parts of α-chloro-o-cresyl N-methylcarbamate in 100 parts of methanol was added 2.7 parts of sodium methylate in 200 parts of methanol at 25° Centigrade. Volhard titration showed that the theoretical amount of sodium chloride had been formed. After 15 hours, the solvent was evaporated. The product was found by infrared and nitrogen analysis to be a mixture of α-methoxy-o-cresyl N-methylcarbamate and α-methoxy-o-cresol. To replace the lost N-methylcarbamate groups, 5 parts of methyl isocyanate plus 0.01 part of dibutyltin laurate catalyst was added, the mixture let stand overnight, and stripped free of isocyanate at 110° and 0.1 mm., leaving the desired carbamate as a light tan syrup.

Anal. Calcd. for $C_{10}H_{13}ON$: N, 7.18; Found: N, 7.01.

In a similar manner other α-lower alkoxy-o-cresyl N-methylcarbamates may be prepared, such as the ethoxy, propoxy, isopropoxy, butoxy or pentoxy compounds.

In an analogous manner, α-(2-methoxyethoxy)-o-cresyl N-methylcarbamate and α-(2-methoxyethoxy)-o-cresol were prepared from α-chloro-o-cresyl N-methyl carbamate and sodium 2-methoxyethoxide, α-furfuryloxy-o-cresyl N-methylcarbamate and α-furfuryloxy-o-cresol were prepared from α-chloro-o-cresyl N-methylcarbamate and sodium furfuroxide. α-Aryloxy phenols and carbamates therefrom are made analogously.

EXAMPLE 88

α-(2.4-Dichlorophenoxy)-o-cresol and N-Methylcarbamate

A solution of 50 parts of α-chloro-o-cresyl N-methylcarbamate and 45 parts of sodium 2,4-dichlorophenate in 200 parts of methyl ethyl ketone was held at 40°–50° for 2 hours. The mixture was cooled, diluted with hexane, and filtered to obtain colorless crystals, m.p. 131.5°–132° C, showing the characteristic infrared carbamate bands.

Anal. Calcd. for $C_{15}H_{13}O_3NCl_2$: N, 4.29; Found: N, 4.26.

Upon heating of the carbamate at 160° C in the presence of 0.1 percent dibutyltin laurate catalyst and passing of a slow nitrogen stream through the melt to sweep out the evolved methyl isocyanate, the above carbamate was caused to revert to the parent α-(2,4-dichlorophenoxy)-o-cresol, a colorless solid, neutralization equivalent (potentiometric titration by tetrabutylammonium hydroxide in puridine solution) 269 mg/milliequivalent.

In an analogous manner, α-chloro-o-cresyl N-methylcarbamate is converted to α-phenoxy-o-cresyl N-methylcarbamate (by reaction with sodium phenoxide), to α-(4-nitrophenoxy)-o-cresyl N-methylcarbamate (by reaction with sodium p-nitrophenoxide), to α-(2,4-dinitrophenoxy)-o-cresyl N-methylcarbamate (by reaction with sodium 2,4-dinitrophenoxide), to α-(2,4,5-trichlorophenoxy)-o-cresyl N-methylcarbamate (by reaction with sodium 2,4,5-trichlorophenoxide), and to α-(pentachlorophenoxy)-o-cresyl N-methylcarbamate (by reaction with potassium pentachlorophenate). Similarly, α-chloro-3,5-xylenyl N-methylcarbamate is converted to α-phenoxy-3,5-xylenyl N-methylcarbamate by reaction with sodium phenoxide. Similarly α-4-dichloro-o-cresyl N,N-dimethylcarbamate is converted to α-(2,4-dichlorophenoxy)-4-chloro-o-cresyl N,N-dimethylcarbamate (by reaction with potassium 2,4-dichlorophenoxide).

The α-hydrocarbyloxyalkylphenyl carbamates thus prepared are pesticidally active. For example, houseflies dipped in a 0.1 percent aqueous dispersion of α-phenoxy-o-cresyl N-methylcarbamate showed 100 percent mortality in 24 hours.

Furthermore, the α-haloalkylphenylhaloformates of the invention can be converted to α-haloalkylphenyl esters and phenols which upon reaction with amines yield α-aminoalkylphenyl derivatives, as illustrated by the following example:

EXAMPLE 89

N-(o-Hydroxybenzyl)pyridinium Chloride N'-Methylcarbamate

A solution of 10 parts of α-chloro-o-cresyl N-methylcarbamate and 3.9 parts of pyridine in 40 parts of ethanol is allowed to stand for 6 days at 30°–50° C, until Volhard titration indicates that the theoretical amount of chloride ion is evolved. The solution was then evaporated to 100° (10 mm.) leaving 12.3 parts of a viscous water soluble syrup having the theoretical percent nitrogen and ionic chloride.

In an analogous manner, α-chloro-o-cresyl N-methylcarbamate and trimethylamine (20 percent alcoholic solution) yield α-trimethylammonio-o-cresyl N-methylcarbamate chloride, α-bromo-p-cresyl N,N-dimethylcarbamate and triethylamine yield α-triethylammonio-p-cresyl N,N-dimethylcarbamate bromide, α,2,4-trichloro-o-cresyl N-(3,4-dichlorophenyl)carbamate and dimethylamine yield α-dimethylamino-2,4-dichloro-o-cresyl N-(3,4-dichlorophenyl)carbamate, α, α'-dichloro-3,5-xylenyl N-methylcarbamate and aniline yield α, α'-dianilino-3,5-xylenyl N-methyl carbamate, α-chloro-o-cresyl N-methylcarbamate and N,N-dimethyl-N-laurylamine yield α-N,N-dimethyl-N-laurylammonio-o-cresyl N'-methylcarbamate chloride, to cite a few illustrative examples. These compounds are pesticidal. The last named quaternary ammonium compound and its N-higher alkyl homologs are strong germicides, producing inhibition of the growth of Staphyllococcus aureus at 0.001 percent concentration in a nutrient agar. Furthermore, α-(N-loweralkylamino)-o-cresyl N-methylcarbamates can be acylated to highly insecticidal α-(N-loweralkyl-N-acylamino)-o-cresyl N-methylcarbamates.

Another group of useful pesticidal derivatives which are rendered synthetically accessible via the novel haloalkylphenylchloroformates of the invention are the haloalkylphenyl alkyl or aryl carbonates, i.e., unsymmetrical esters of carbonic acid, one esterifying moiety being the haloalkylphenyl group. In general these may be prepared by reaction of an alcohol or an alcoholate with the desired haloalkylphenyl chloroformate. The thiol analogs may be prepared analogously, using mercaptides as reactants.

EXAMPLE 90

A mixture of 5 parts of α, α-dichloro-3,4-xylenyl chloroformate and 40 parts of methanol were admixed. A mild spontaneous exotherm occurred. After 10 hours, the mixture was distilled free of unreacted alcohol and hydrogen chloride by applying a vacuum (ultimately 0.2 mm.) and raising the temperature gradually to 100°. The product was obtained as a residual light yellowish oil.

Anal. Calcd. for $C_{10}H_{10}O_3Cl_2$: Cl, 28.5; Found: Cl, 28.6.

In the same manner, the following carbonates were made. In every case the product was a liquid.

| Chloroformate Used | Alcohol Used | Carbonate Made | % Chlorine Theory | Found |
|---|---|---|---|---|
| α-chloro-o-cresyl | ethanol | ethyl-α-chloro-o-cresyl | 16.5 | 16.4 |
| α-chloro-o-cresyl | isopropanol | isopropyl-α-chloro-o-cresyl | 15.5 | 15.3 |
| α-chloro-o-cresyl | n-butanol | n-butyl-α-chloro-o-cresyl | 14.6 | 14.1 |
| α-chloro-o-cresyl | 2-methoxyethanol | 2-methoxyethyl α-chloro-o-cresyl | 14.4 | 14.5 |
| α-chloro-o-cresyl | n-amyl | n-amyl-α-chloro-o-cresyl | 13.8 | 13.4 |
| α,α'-dichloro-3,5-xylenyl | methanol | methyl-α,α'-dichloro-3,5-xylenyl | 28.5 | 28.4 |
| α,α'-dichloro-3,5-xylenyl | ethanol | ethyl-α,α'-dichloro-3,5-xylenyl | 27.0 | 27.0 |
| α,α'-dichloro-3,5-xylenyl | isopropanol | isopropyl α,α'-dichloro-3,5-xylenyl | 25.6 | 26.0 |
| α,α'-dichloro-3,5-xylenyl | 2-methoxyethanol | 2-methoxyethyl-α,α'-dichloro-3,5-xylenyl | 24.2 | 23.6 |
| α,α'-dichloro-3,5-xylenyl | n-butanol | n-butyl α,α'-dichloro-3,5-xylenyl | 24.4 | 23.7 |
| α,α'-dichloro-3,5-xylenyl | n-amyl | n-amyl α,α'-dichloro-3,5-xylenyl | 23.5 | 23.3 |
| α,α'-dichloro-3,5-xylenyl | ethyl mercaptan | S-ethyl α,α'-dichloro-3,5-xylenyl* | | |
| α,α'-dichloro-3,5-xylenyl | 2-chloroethanol | 2-chloroethyl α,α'-dichloro-3,5-xylenyl | 35.7 | 35.0 |
| α,α',α'-trichloro-3,5-xylenyl | methanol | methyl α,α',α'-trichloro-3,5-xylenyl | 37.5 | 34.2 |
| α,α,α',α'-tetrachloro-3,5-xylenyl | methanol | methyl α,α,α',α'-tetrachloro-3,5-xylenyl | 44.6 | 44.0 |
| α-chloro-o-cresyl | 2-chloroethanol | 2-chloroethyl α-chloro-o-cresyl | 28.5 | 27.9 |

*thiolcarbonate

In a similar manner the following ring-halogenateed side-chain halogenated aryl carbonates were made:

| Chlorofomate Used | Alcohol Used | Carbonate Made |
|---|---|---|
| α-bromo-3-chloro-p-cresyl | methanol | methyl α-bromo-3-chloro p-cresyl |
| α,3,4,5,6-pentachloro-o-cresyl | methanol | methyl α,3,4,5,6-pentachloro-o-cresyl |
| α,α,2,4-tetrachloro-3,5-xylenyl | ethanol | ethyl α,α',2,4-tetrachloro-3,5-xylenyl |
| α,2,4,6-tetrachloro-3,5-xylenyl | n-butanol | n-butyl α,2,4,6-tetrachloro-3,5-xylenyl |
| α,α,α',α',2,4-hexachloro-3,5-xylenyl | isopropyl | isopropyl α,α,α',α',2,4-hexachloro-3,5-xylenyl |
| α-chloro-2,4-dichloro-o-cresyl | phenol* | phenyl α-chloro-2,4- |

-continued

| Chlorofomate Used | Alcohol Used | Carbonate Made |
|---|---|---|
| α,2-dichloro-p-cresyl | p-nitrophenol* | dichloro-o-cresyl p-nitrophenyl α,2-dichloro-p-cresyl |

*in presence of 1 molar equivalent of triethylamine, in dioxane solvent

These carbonates were found to be useful inter alia as herbicides. For example, methyl α,2,4-trichloro-o-cresyl carbonate applied in aqueous dispersion at the rate of 8 pounds per acre to crabgrass seedlings produced 100 percent mortality in 1 week. Isopropyl α, α, α', α',2,4-hexachloro-3,5-xylenyl carbonate sprayed in aqueous dispersion at the rate of 8 pounds per acre to a mixed population of ragweed and pigweed produced complete kill in 10 days.

Another group of useful insecticidal derivatives which can be prepared from the novel haloalkylphenyl chloroformates of the invention are the phosphorothioates of the structure Aryl-O—CO—SPS(O-alkyl)$_2$, wherein the aryl residue is that derived from the haloalkylphenyl chloroformate. Since the side-chain halogen is reactive, it may be further displaced by a second —SPS(O-alkyl)$_2$ group. Both of these classes of derivatives exhibit useful insecticidal properties.

EXAMPLE 91

Preparation of Unsymmetrical Thioanhydride of α-chloro-o-cresyl Carbonic Acid and O,O-dimethylphosphorodithioic Acid A mixture of 10.25 parts of α-chloro-o-cresyl chloroformate and 9 parts of sodium O,C-dimethylphosphorodithioate in 20 parts of methyl ethyl ketone was allowed to warm spontaneously to 35°, let stand 10 hours, filtered to remove salt, and evaporated to remove solvent, leaving the product as a reddish oil. The infrared spectrum showed a carbonyl band at 5.72μ establishing that the —CoCl function had reacted and that a new carbonyl structure had formed.

Anal. Calcd. for $C_{10}H_{12}O_4S_2PCl$: P, 9.99; Found: P, 9.88.

This product, sprayed at 0.1 percent in aqueous dispersion onto black bean aphids produced 95 percent aphid mortality in 48 hours.

In a like manner, p-Cl$_3$C—C$_4$H$_4$—O—CO—SP-S(OCH$_3$)$_2$ and p-(CH$_3$O)$_2$ PS-SCH$_2$C$_6$H$_4$O-CO-SPS(OCH$_3$)$_2$ are prepared from α, α, α-trichloro-p-cresyl chloroformate to α-bromo-p-cresyl chloroformate and one or two molar equivalents, respectively, of sodium O,O-dimethyl phosphorodithiolate.

The α, α'-dichloro-2,3-xylenyl and α, α'-dichloro-3,4-xylenyl chloroformates have the special advantage of permitting conversion to valuable heterocyclic systems not otherwise readily obtainable. For instance, they may be converted to α, α'-dichloro-2,3- and -3,4-xylenyl carbamates or other esters which then may be reacted with ammonia or primary amines to form dihydroisoindolyl esters, or with aqueous bases to form phthalanols or phthalanyl esters, or with sulfide anion to form thiophthalanols or thiophthalanyl esters (dihydroisothianathenols or dihydroisothianaphthenyl esters). The N-methylcarbamates of these heterocyclic phenols are highly insecticidal and also nematocidal.

EXAMPLE 92

1,3-Dihydroisothianaphthen-4-yl N-Methylcarbamate

A solution of 10 parts of α, α'-dichloro-2,3-xylenyl N-methylcarbamate and 5.5 parts of 60 percent sodium sulfide (commercial flaked hydrate) in 200 parts ethyl alcohol was stirred 15 hours at 30°–33°, then an aliquot was titrated for chloride, which showed all the available α-chlorine to have been released as chloride ion. The mixture was filtered, evaporated to dryness, and the residue examined by infrared. It was found to contain 1,3-dihydroisothianaphthenol (OH band) as well as the carbamate (C=O band). Therefore the residue was dissolved in tetrahydrofuran, treated with 5 parts of methyl isocyanate, re-evaporated and recrystallized from benzene-methanol to obtain the desired N-methylcarbamate as a colorless solid, m.p. 115°–117°.

Anal. Calcd. for $C_{10}H_{11}O_2NS$: N, 6.7, S, 15.3; Found: N, 6.5, S, 15.5

This compound, sprayed at 0.1 percent in aqueous dispersion on larvae of the Mexican bean beetle, produced 100 percent insect mortality in 48 hours.

EXAMPLE 93

1,3-Dihydroisothianaphtlen-5-yl N-Methylcarbamate

A procedure identical to the preceding example was used to convert α, α'-dichloro-3,4-xylenyl N-methylcarbamate. The product, recrystallized from aqueous methanol, was a colorless solid, m.p. 133°–135°.

Anal. Calcd. for $C_{10}H_{11}O_2NS$: N, 6.7; Found: N, 6.4.

This compound as well as the isomer of the preceding example when admixed with nematode-infested soil at 147 pounds per acre gave complete prevention of nematode-caused root knotting of cucumber seedlings planted in the treated soil.

The acid halides of the invention are also useful as chemical intermediates for the synthesis of side-chain halogenated phenols not otherwise accessible. For example, careful hydrolysis of α, α-dichloro-o-, m-, or p-cresyl chloroformate by adding one molar equivalent of water (conveniently in a co-solvent such as dioxane) at 0° to 60° yields α, α-dichloro-o-, m-, or p-cresyl all hitherto unknown; α, α, α-trichloro-o-, m-, or p-cresyl chloroformate on hydrolysis yields similarly α, α, α-trichloro-o-, m-, or p-cresol all hitherto unknown; α-chloro-m-cresyl chloroformate similarly on careful hydrolysis yields α-chloro-m-cresol, hitherto unknown. Such side-chain halogenated phenols have only existed before in the form of their esters which however cannot be hydrolyzed to the phenols themselves without destruction of the labile haloalkyl side chain.

More extensive hydrolysis of the compounds of the invention yields phenols substituted with HOCH$_2$—, O=CH—, and HOC(=O)— groups. While many of these are known, the route to them via the compounds of the invention is in many cases more economical than the synthetic methods of the prior art. Thus α, α-dichloro-o-cresyl chloroformate may be hydrolyzed to salicylaldehyde, a useful perfume ingredient, and α, α, α-trichloro-o-cresyl chloroformate may be hydrolyzed to salicyclic acid, a useful drug.

EXAMPLE 94

Chloromethylation of 3,5-Xylenyl Chloroformate

Into a stirred mixture of 37 parts of 3.5-xylenyl chloroformate, 78 parts of paraformaldehyde, 10 parts of powdered anhydrous zinc chloride, and 150 parts of chloroform at 20°-30° Centigrade, was passed hydrogen chloride gas over 10½ hours. The paraformaldehyde slowly dissolved. Then the reaction mixture was agitated briefly with ice water, after which the organic layer was decanted, dried over magnesium sulfate, filtered, and solvent was evaporated off. The residual liquid was distilled to obtain 17 parts of chloromethyl-3,5-dimethylphenyl chloroformate, b.p. 80°-85° (0.005 mm.) in which the position of the chloromethyl group is indicated to be mostly para.

Anal. Calcd. for $C_{10}H_{10}O_2Cl_2$: Cl, 30.4; Found: Cl, 30.2.

In the same manner, p-cresyl chloroformate is chloromethylated to produce 2-(chloromethyl)-p-cresyl chloroformate, 2,3,5,6-tetramethylphenyl chloroformate is chloromethylated to produce 4-chloromethyl-2,3,5,6-tetramethylphenyl chloroformate, and α-cyclopentylphenyl chloroformate is chloromethylated to produce 4-chloromethyl-2-cyclopentylphenyl chloroformate.

EXAMPLE 95

Nematocidal Use

Soil infested with nematodes of the species *Meloidogyne incognita* was admixed at the rate of 200 parts per million with α, α'-dichloro-2,3-xylenyl N-methylcarbamate. Then cucumber seedlings were planted in the treated soil and allowed to grow for two weeks. The seedlings were then uprooted and the roots examined for nematode-caused root knots, which were found to be substantially absent. By contrast, similar seedlings grown in the infested soil without the nematocidal treatment exhibited roots which were all heavily damaged by nematode-caused root knots.

EXAMPLE 96

Activity on Houseflies

Adult houseflies (*Musca domestica*) were treated with 0.1 percent aqueous dispersions of various of the N-methylcarbamate compounds of the invention and various known carbamates. The percentage knockdown at 2 hours and percentage kill at 24 hours were as follows:

| N-Methylcarbamate | 2 Hour Knockdown | 24 Hour Kill |
| --- | --- | --- |
| α,α-dichloro-o-cresyl | 100 | 100 |
| α,α-dichloro-m-cresyl | 100 | 100 |
| 2-(2,3-dichloropropyl)phenyl | 100 | 100 |
| 2-(1,2,3-trichloropropyl)phenyl | 95 | 100 |
| o-cresyl | 80 | 40 |
| m-cresyl | 85 | 75 |

EXAMPLE 97

Herbicidal Activity

Onto a mixed population of ragweed, lambsquarters, and pigweed is sprayed an aqueous dispersion of α,4,6-trichloro-o-cresyl N,N-dimethylcarbamate (with the aid of a solvent quantity of xylene plus Emxol H500X, a blended polyoxyethylene ether/alkylarylsulfonate emulsifier) at the rate of 8 pounds of the carbamate per acre. Within 1 week, substantially complete weed kill is observed.

Similar results are obtained during α,4,6-trichloro-o-cresyl 1-morpholinecarboxylate as the active ingredient of the spray at the same rate.

EXAMPLE 98

Bacteriostatic Activity

These carbamates, especially the N-arylcarbamates, are also active antibacterial compounds. A nutrient agar was admixed with 100 parts per million by weight of various of the carbamates of the invention and then inoculated with spores of *Staphylococcus aureus*. The growth or absence of growth of bacterial colonies was noted in 3 days. The chemicals thus tested are shown in the table below:

| Chemical | Degree of Inhibition |
| --- | --- |
| α,α,α-trichloro-o-cresyl N-(p-chlorophenyl)carbamate | + |
| α,α'-dichloro-o-cresyl N-(p-nitrophenyl)carbamate | + |
| α,α,α-trichloro-o-cresyl N-(3,4-dichlorophenyl)carbamate | + |
| α,α,4-trichloro-o-cresyl N-(p-chlorophenyl)carbamate | + |
| α-chloro-2-isopropylphenyl N-phenylcarbamate | + |
| α,α,4,6-tetrachloro-o-cresyl N-1-naphthylcarbamate | + |
| α-chloro-p-cresyl N-methylcarbmate | ± |
| p-cresyl N-methylcarbamate | − |

Key:
+ = growth largely prevented,
± = border line action,
− = no inhibition

While there have been described various embodiments of the invention, the methods and elements described are not intended to be understood as limiting the scope of the invention, as it is realized that changes therewithin are possible, and it is further intended that each element recited in any of the following claims is to be understood as referring to all equivalent elements for accomplishing substantially the same results in substantially the same or equivalent manner, it being intended to cover the invention broadly in whatever form its principle may be utilized.

I claim:

1. The compound of the formula

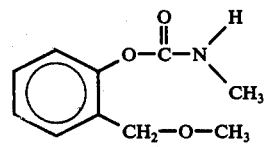

* * * * *

UNITED STATES PATENT OFFICE
CERTIFICATE OF CORRECTION

Patent No. 4,059,615    Dated November 22, 1977

Inventor(s) Edward D. Weil

It is certified that error appears in the above-identified patent and that said Letters Patent are hereby corrected as shown below:

Column 1, line 60, formula "$I'_b$" should read ---$X'_b$---. Column 2, line 40, formula "$I'_b$" should read ---$X'_b$---. Col. 3, line 1, "1 halogen atoms" should read ---1 halogen atom---; line 15, "$I'_b$" should read ---$X'_b$---; formula 5, "$HBr_2$" should read ---$CHBr_2$---. Column 13, line 59, "anhydrous chloride" should read ---anhydrous hydrogen chloride---. Col. 15, line 9, "kerosene along" should read ---kerosene alone---. Column 15, line 32, "other linkages" should read ---ether linkages---. Column 16, line 17, "perticidal" should read ---pesticidal---; Example 30, Empirical Formula "$C_8 H_8 C NCl$" should read ---$C_8 H_8 O NCl$---; Example 31, Physical Properties, "crystals 108-m.p. 110°C" should read ---crystals m.p. 108-110°C---. Column 17, Example 40, Physical Properties "undistill-$C_{14} H_{20} O_2 NCl$ able tan syrup" should read ---undistillable tan syrup $C_{14} H_{20} O_2 NCl$---.

UNITED STATES PATENT OFFICE
CERTIFICATE OF CORRECTION

Patent No. 4,059,615      Dated November 22, 1977

Inventor(s) Edward D. Weil

It is certified that error appears in the above-identified patent and that said Letters Patent are hereby corrected as shown below:

Column 21, line 23, "free phanol" should read ---free phenol---
Column 26, line 55, "halogenateed" should read ---halogenated---. Column 28, line 32, "Dihydroisothianaphtlen-5-yl" should read ---Dihydroisothianaphthen-5-yl---.

Signed and Sealed this

Twenty-first Day of November 1978

[SEAL]

Attest:

RUTH C. MASON
Attesting Officer

DONALD W. BANNER
Commissioner of Patents and Trademarks